United States Patent [19]

Gurler

[11] Patent Number: 5,469,146

[45] Date of Patent: Nov. 21, 1995

[54] DEVICE FOR ATTACHING TO AND DETECTING WETNESS IN DIAPERS

[76] Inventor: Yener Gurler, 273 Saint Henry Dr., Fremont, Calif. 94539

[21] Appl. No.: 289,515

[22] Filed: Aug. 12, 1994

[51] Int. Cl.[6] .................................................. G08B 21/00
[52] U.S. Cl. ........................ 340/605; 340/604; 340/602; 340/539; 200/61.05; 128/886
[58] Field of Search .................................. 340/605, 602, 340/604, 539, 573, 693; 604/361; 128/886; 200/61.05; 24/528

[56] References Cited

U.S. PATENT DOCUMENTS

| | | | |
|---|---|---|---|
| 3,508,235 | 4/1970 | Baisden | 340/235 |
| 3,678,928 | 7/1972 | Mozes | 128/138 |
| 4,106,001 | 8/1978 | Mahoney | 340/604 |
| 4,191,950 | 3/1980 | Levin et al. | 340/604 |
| 4,484,573 | 11/1984 | Yoo | 128/138 A |
| 4,539,559 | 9/1985 | Kelly et al. | 340/573 |
| 4,640,276 | 2/1987 | Jing-Sheng | 128/138 A |
| 4,768,023 | 8/1988 | Xie | 340/573 |
| 4,796,014 | 1/1989 | Chia | 340/573 |

*Primary Examiner*—John K. Peng
*Assistant Examiner*—Julie B. Lieu

[57] ABSTRACT

A device for attaching to and detecting wetness in diapers. The device including a pair of probes (28) supported on a module box (10) slidably mounted between the guides (36) of a slide section (34). The device is attachable to the diaper (56) by sliding the module box (10) toward the slide section (34) such as to trap a fold of the fabric item between the probes (28) and the slide section (34). The module box (10) contains a signal circuit (14) which is activated when wetness is present between the probes (28) in the fold of the fabric item. The signal can be a melody playing IC chip or LCD time display, or both.

13 Claims, 3 Drawing Sheets

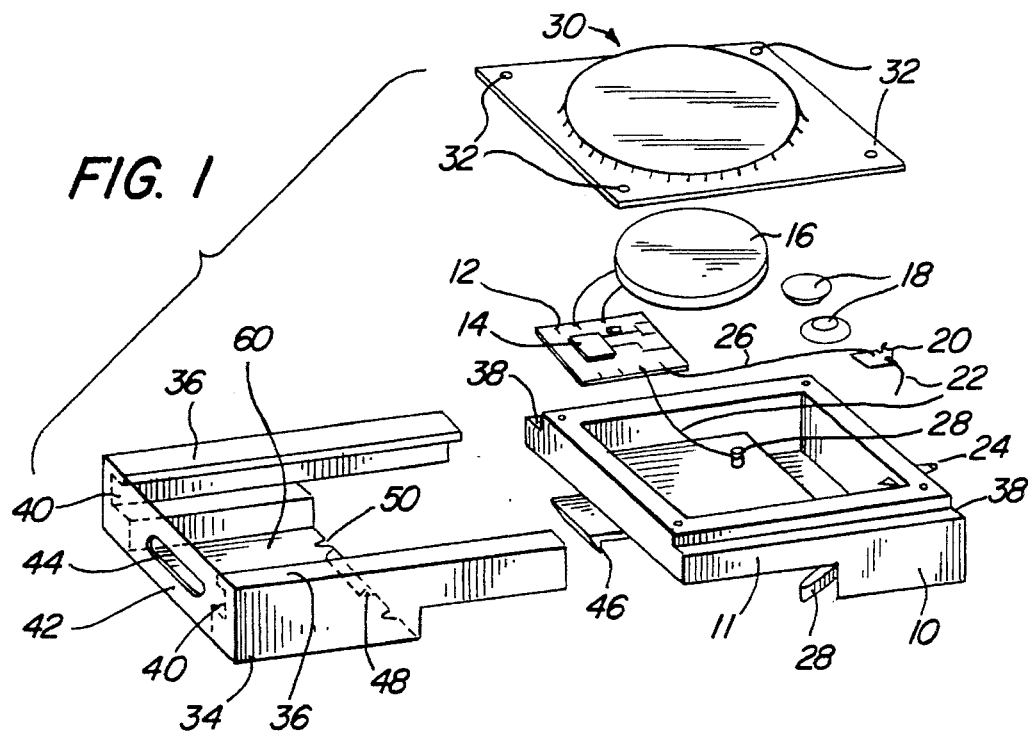
FIG. 1
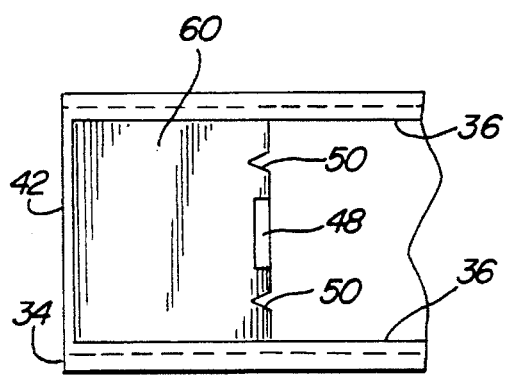
FIG. 2
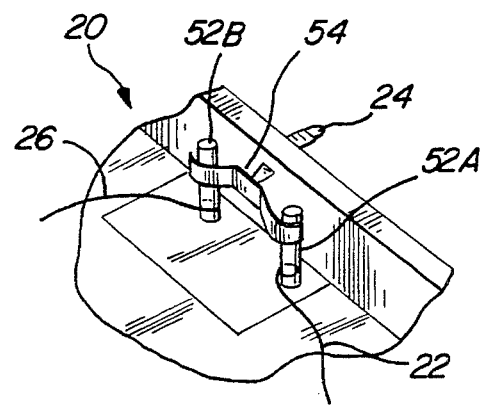
FIG. 3
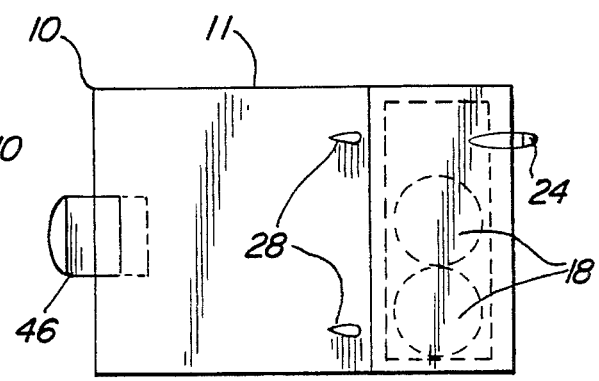
FIG. 4
FIG. 5

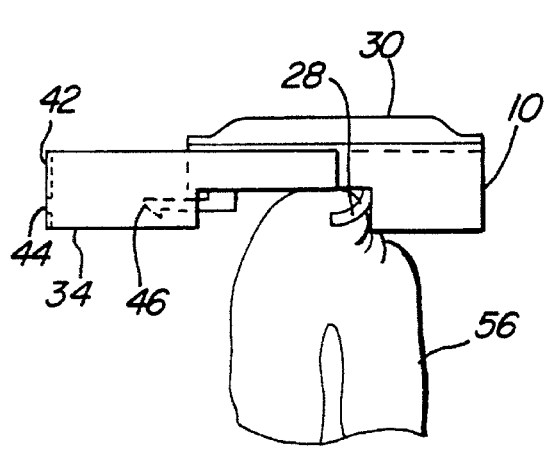
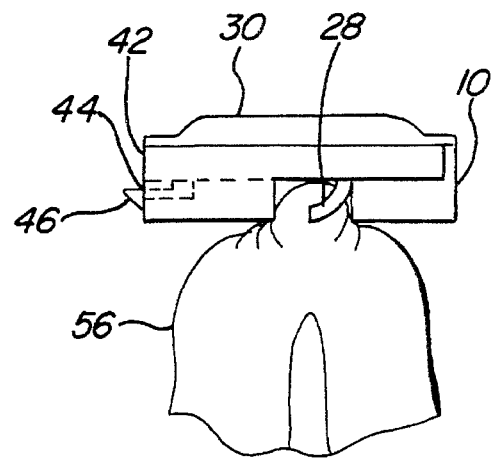
FIG. 6A    FIG. 6B
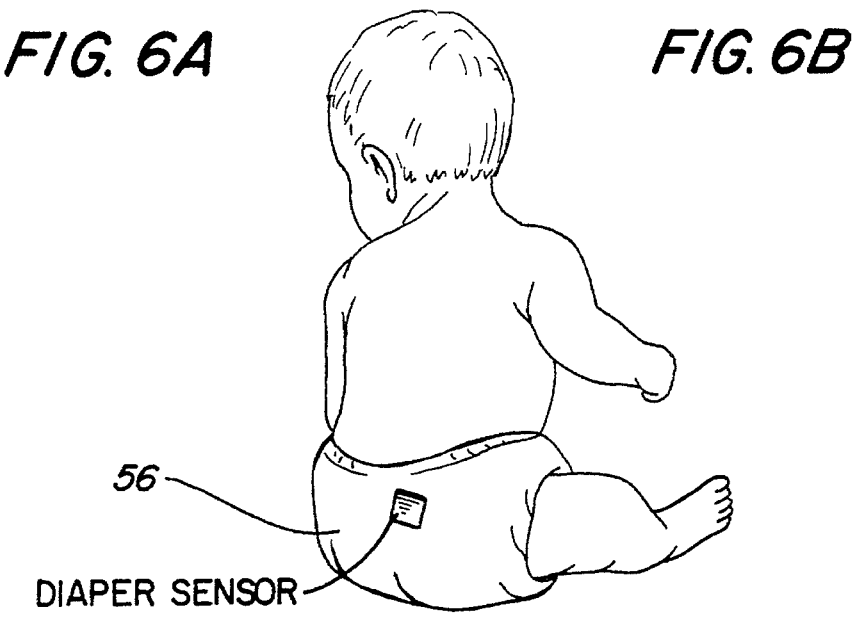
DIAPER SENSOR
FIG. 7
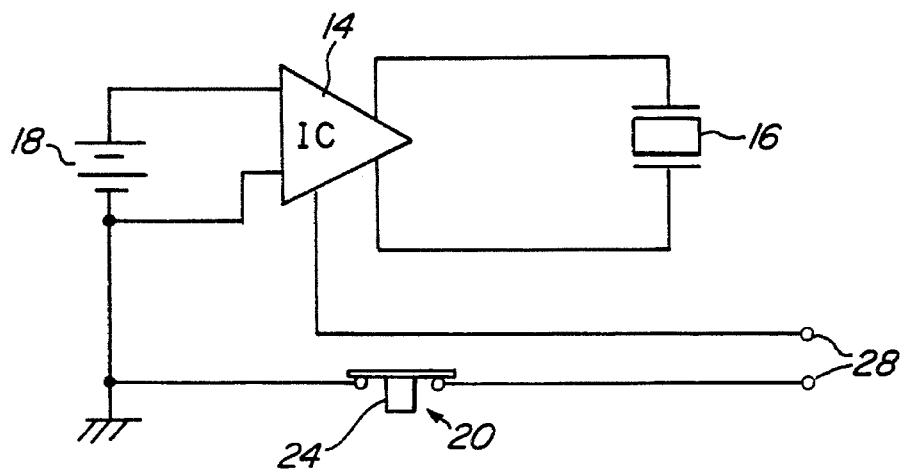
FIG. 8

DEVICE FOR ATTACHING TO AND DETECTING WETNESS IN DIAPERS

FIELD OF THE INVENTION

This invention relates to sensing devices which sound alarms such as a buzzer or activates a visual display to indicate when the garment to which it has been attached becomes damp and particularly to a device that is attachable directly to the outside of a plastic covered diaper, has a repetitive signal feature for confirming wetness and sensitivity of the response to wetness depends on conductivity between two electrical probes.

BACKGROUND OF THE INVENTION

Diaper rash on infants and bed ridden elderly people is well known to be a painful condition. Although there are medications on the market to cure diaper rash, the person continues to suffer until cured unless it is further aggravated by contact with soiled diapers in which case it takes longer.

To prevent diaper rash, the best thing to do is to remove the soiled diaper, clean the areas affected by urine and excrement from the person's body and replace the diaper as soon as possible. The importance of this subject is indicated by the numerous devices invented and patents granted for them.

U.S. Pat. No. 3,508,235 to Baisden is for a device including two pins or separate sections of a single pin comprising dissimilar metals which generate a galvanic potential when wet. One disadvantage of this invention is the high cost of manufacture of the pin structure as described as well as the impracticality of pushing a pin into the diaper to come out at a point because inner padding does not allow the pin to be pushed through it.

U.S. Pat. No. 3,678,928 to Mozes is for a device supported by a waist belt and gives a stimulus to the user in case of unintentional urination. It is for adults and impractical for infants.

U.S. Pat. No. 4,106,001 to Mahoney is for a device with an audio alarm in a housing attached to the undergarment with strip conductors attached to the outside of the garment and the housing by adhesive for use as a warning in case of unintentional urination Again not applicable for use on infants' diapers.

U.S. Pat. No. 4,191,950 to Levin et al is for an anti bed wetting device. Not applicable for use on infants' diapers and rather cumbersome to attach and use.

U.S. Pat. No. 4,640,276 to Jing-Sheng comprises an alarm system with audio source attachable by adhesive tape inside a diaper as well as having holes on the box, which makes the system extremely unhygenic. No practical means of attachment to the outside of diaper is proposed.

U.S. Pat. No. 4,484,573 to Yoo is for an alarm device having an electronic circuit on a board with two ring-shaped detecting pans mounted concentrically and connected electrically to the circuit which are placed directly inside the diaper. For attachment, rather unsafe and impractical tie rings are provided for tying the device which can easily fall off or be pulled off.

U.S. Pat. No. 4,539,559 to Kelly is for a portable electronic signaling device with a disposable sensor strip to be attached onto undergarment or put inside the diaper. The disadvantage of an unsafe strip of electrodes inside the diaper is obvious.

U.S. Pat. No. 4,768,023 to Xie is for a disposable diaper containing a pair of imbedded electrodes terminated by conductive and adhesive tapes. This type of sensing device needs to be constructed by diaper manufacturer otherwise pushing electrodes into the diaper padding is absolutely impractical.

U.S. Pat. No. 4,796,014 to Chia is for a urine detecting device mounted on a safety pin. This device also has the disadvantages of costly construction of nonconducting safety pins coated with two conductors, as well as impracticality of inserting safety pin into the diaper padding.

Therefore, all of the foregoing inventions have at least one disadvantage including problems with tile use of safety pins which are dangerous and impractical to push through a disposable diaper, use of an unreliable or messy adhesive, a requirement to locate tile sensor of the device inside the diaper, a persistent signal that arouses the infant when the infant is sleeping, and no indication of the time of exposure of the infant to the urine soaked diaper.

SUMMARY OF THE INVENTION

It is an object of this invention to provide a device for alerting an attendant that release of urine has occurred such as to soil the diaper or undergarment of the wearer.

It is an object that the device disturb the wearer as little as possible; therefore, in one embodiment, the device includes an audible alarm that emits a sound of short duration so as not to arouse a sleeping infant. The sound may be a short melody. A variation of this embodiment is a switch button that an attendant depresses momentarily to repeat the signal and thereby confirm that the diaper is wet.

It is a further object that the device be compatible in an environment including a room with a number of infants or patients so that, instead of an audible alarm, a visual display alerts the attendant so as not to arouse a sleeping infant or its companions.

In another variation, the display includes a counter that displays the elapsed time that the diaper has been wet, since this information may be a useful guide in diagnosing and prescribing treatment for the infant or patient.

It is a further object that the circuit be operated with a low power requirement. To this end, the means for providing the audio signal is a melody provided by a programmable edge triggered single or double tone melody generator integrated circuit such as TMA 224, HM5801, HM5811A available at an extremely low cost from Hong Kong and Taiwan manufacturers of melody IC's.

The device features a pair of electrodes mounted to slide on a housing such that the electrodes slide toward a base and capture a fold of the diaper between the electrodes and base. Commercial disposable diapers typically include an inner lining that absorbs the urine and an outer coveting which is made of thin plastic to contain the wet absorbent padding. The electrodes are shaped to pierce the outside plastic cover of the diaper so that the device can be conveniently secured to the outside of the diaper in contrast to devices of the prior art that require positioning inside the diaper.

Although the foregoing application is described as used on a disposable diaper, it can be used just as well on washable cloth diapers or as an alarm system on any cloth which can become wet by any leaking electrically conducting liquid.

BRIEF DESCRIPTION OF THE DRAWINGS

FIG. 1 is an exploded view of a preferred embodiment.

FIG. 2 is a cutaway view showing the slide section and module box fitted together.

FIG. 3 is a bottom view of the module box.

FIG. 4 is a top view of the slide section.

FIG. 5 shows the reset switch in detail.

FIG. 6 A and B show the method of attaching the device to the diaper.

FIG. 7 shows the baby wearing a diaper with the device of this invention.

FIG. 8 shows the schematic circuit of the invention, melody only.

REFERENCE NUMERALS IN DRAWINGS

Figure 11A:
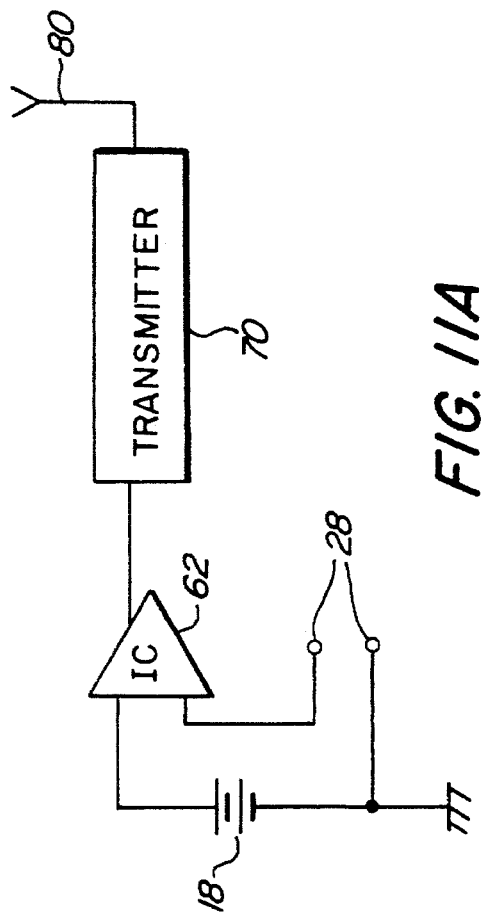
FIGS 11A and 11B show a schematic representation of an alternative embodiment of the present invention.

| | |
|---|---|
| 10 Module box | 16 Piezolectric buzzer |
| 12 Circuit board | 18 Batteries |
| 14 Integrated circuit IC(HM 5801 or equivalent) | 20 Reset switch |
| | 46 Catch |
| | 48 Latch |
| 22 Wire connection | 50 V grooves |
| 24 Push button | 52 Posts |
| 26 Wire connection | 54 Spring contact |
| 28 Sensor probes | 56 Diaper |
| 30 Lid | 58 "O" ring |
| 32 Screw holes | 60 Bottom of slide section |
| 34 Slide section | 62 IC (HM 5801A or equivalent) |
| 36 Guide | 64 CPU, IC (LC 5851 or equivalent) |
| 38 Shoulder | 66 Liquid crystal display (LCD) |
| 40 Recess | 68 Light emitting diode (LED) |
| 42 End cover | |
| 44 Slot | |

DESCRIPTION OF A PREFERRED EMBODIMENT

Turning now to a discussion of the drawings, FIG. 1 is an exploded view of a preferred embodiment showing a module box, 10, which houses a circuit board, 12, with integrated circuit, 14. To the board, 12, are attached piezoelectric "buzzer", 16, (used as speaker), batteries 18, and probe connection wires, 22, one of which is connected to board, 12, through a normally closed spring switch, 20, and wire, 26. The wires, 22, are connected to the stems of the sensor probes, 28, inside the module box, 10. The module box 10 further has an under surface 11, which serves as means for supporting the probes 28. The lid, 30, is made of metal and is slightly coined to house the buzzer, 16, (for a good reasonance and loud enough melody sound) and is secured onto the module box, 10, by screws through the screw holes, 32.

As shown in FIG. 2, an "O" ring seal, 58, is interposed between the lid 30 and the module box, 10, which secures waterproof covering. The slide section, 34, has guides, 36, extending inwardly at the top on each side, which slide onto shoulders, 38, on both sides of module box, 10. Recesses, 40, seat the bottom edges of the module box, 10.

FIG. 1 shows the end of slide section, 34, having an end cover, 42, with a slot, 44, which engages catch, 46, which is attached to module box, 10. A bottom view of the module box, 10, is shown in FIG. 3.

Catch, 46, is made of spring material and snaps onto slot, 44, such as to detachably engage slide section, 34, to module box, 10. The latch, 48, at the edge of the bottom, 60, of slide section, 34, (FIG. 1) engages catch, 46, when slide section, 34, and module box, 10, are in open position so that they will not be separated. The catch, 46, can be disengaged from latch, 48, by lifting the catch, 46, from engagement with the latch, 48, and pulling the slide section, 34, and module box, 10, apart for cleaning as desired. The "V" grooves, 50, shown in FIG. 4 located at the bottom, 60, of the slide section, 34, are spaced to accommodate the two sensor probes, 28, allowing some diaper material to be trapped inside and in between the "V" grooves to provide good clamping function.

FIG. 5 is a more detailed view of the normally closed switch, 20, used in the preferred embodiment. Two metal posts, 52, are fixed to the base of the module box, 10. One side of the spring contact, 54, is fixed to the post, 52A, which is connected to the probe, 28, by wire, 22, and the other end is free to make/break contact from the post, 52B, which is connected to the circuit, 14, by wire, 26. The contact can be broken by pushing the button, 24, (installed waterproof) from outside the module box, 10, in order to reset the circuit by opening and closing switch, 20, so as to retrigger the circuit, 14. This causes the melody to be replayed if material between the two sensor probes, 28, is conducting, thereby confirming that the diaper is wet.

FIGS. 6A and 6B show the method for attaching the device to the diaper, 56. It is best to connect the device to the diaper before applying the diaper to the infant. To attach the device to the diaper, the diaper is folded at the portion to which the device is to be hooked as shown in FIG. 6A. Then the sensor probes, 28, are pushed into the diaper, 56, piercing the plastic outer covering as shown in FIG. 6B. While the box, 10, is held, the slide, 34, is pushed towards module section, 10, until the spring catch, 46, enters slot, 44, and engages the end cover, 42, so as to lock the slide section, 34, and module box, 10, together securely trapping pan of the diaper, 56, in contact with the sensor pins, 28. FIG. 7 shows the diaper sensor module in use on an infant. The device is removed from the module by lifting catch, 46, thereby disengaging it from the slot, 44, and hence the slide section, 34, and separating by sliding the module box, 10, from the slide section, 34.

FIG. 8 shows a schematic diagram of the circuit described in "Preferred Embodiment". There are shown sensor probes, 28, and push button switch, 20, connected to IC, 14, which is HM5801 or equivalent type "edge triggered melody generator". Batteries, 18, connected to IC, 14, are also shown. Output terminals are connected from the IC to the signaling device. In an embodiment, component, 16, is a piezoelectric buzzer used as a speaker.

Figure 9:
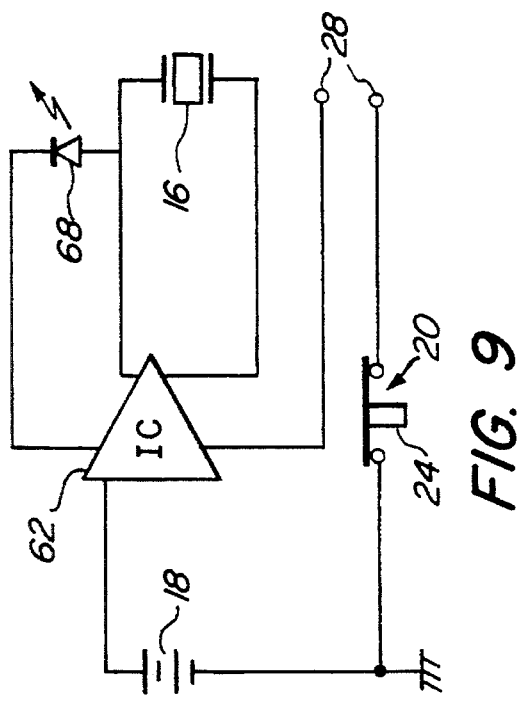
FIG. 9 shows the schematic circuit of the invention, melody and flashing LED.

FIG. 9 shows a schematic of an embodiment where the IC, 62, is type HM 5801A, which has a function to energize an LED, 66, to flash as well as playing melody through the piezoelectric buzzer, 16, thus providing both an audio and visual alarm.

Figure 10:
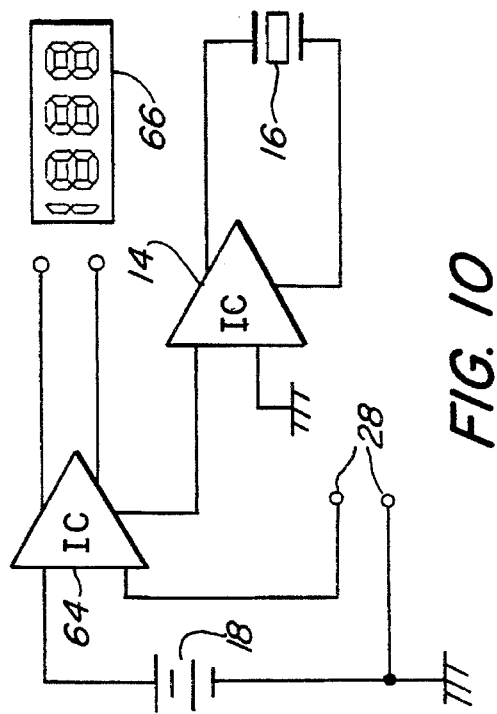
FIG. 10 shows the schematic circuit of the invention, melody and LCD.

FIG. 10 shows a schematic of another combination where the probes, 28, energize a CPU (Central Processing Unit) IC, 64, which in turn drives the melody IC, 14, as well as starts LCD, 66, time counting In this configuration, melody function can also be integrated into IC, 64, eliminating IC, 14.

Figure 11B:
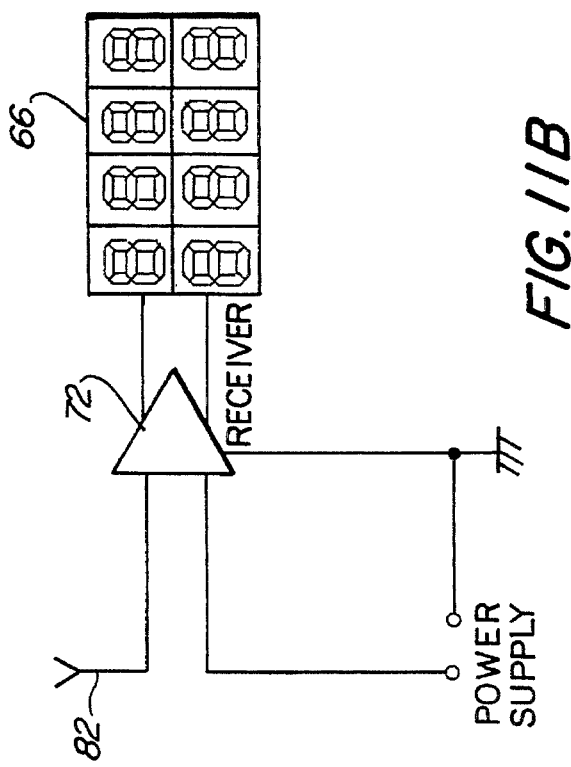

An alternative embodiment of the invention requires triggering of a low power signal transmitter 70 and a remote receiver 72 to sound the alarm and indicator of source 66. FIG. 11A and FIG. 11B show transmitter 70 and receiver 72.

When moisture is detected by probes 28, the transmitter 70 transmits a signal to be detected by receiver 72.

In the preferred embodiment described, IC, 14, is normally on standby state when very low current is always flowing through it as long as the batteries, 18, are connected and the probes, 28, are open circuit or in high resistivity state. When the resistivity between probes, 28, is reduced below a critical value—in this case a few kilo ohms—by increased conductivity with emission of urine into the diaper, IC, 14, is triggered to allow increased current flow thereby IC, 14, is activated to play the melody. On conclusion of the preprogrammed melody of 10–30 seconds duration, IC, 14, goes into a shutdown state. IC, 14, will not be on standby until the probes, 28, become open circuit by removing the device or by emulating this removal by the use of normally closed switch, 20, with push button, 24, which opens one of the probes, 28, then remakes contact when push button is released. This action is cause for replaying the melody when the diaper is wet.

For other embodiments proposed with an LCD time counter, 66, flashing LED, 68, or a transmitter, the circuit will be suitably modified for the additional functions, and additional components will be added inside the module box, 10, housing.

When the component, 16, is accompanied by LCD time counter, 66, it times the period from the instant of wetting until the device is disconnected which also effectively indicates visually that the diaper is wet.

Major features and advantages of the invention include the novel construction whereby two probes having dual functions of electrical sensing as well as providing mechanical lock mechanism by trapping a fold of the diaper against a base surface of a base (the slide section) thereby providing a stronger anchoring mechanism to the diaper than is provided by constructions of the prior art. Other embodiments and variations may be contemplated which are within the scope of the invention. I therefore wish to define the scope of my invention by the appended claims.

I claim:

1. A device for signaling presence of moisture in a fabric item which comprises:
   a module box having a slide section slidably coupled thereto;
   a pair of probes;
   support means for coupling said probes to said module box, said support means supporting said probes at a distance from one another, each of said probes having an end extending downwardly from said module box;
   means for slidably mounting said support means on said slide section, said mounting means integrally coupled to said slide section such that said probes are adapted for trapping a fold of said fabric item between said slide section and said probe ends; and
   means connected to said probes for emitting a signal responsive to conduction of electrical current between said probes, said signal emitting means retained in said module box.

2. A device as in claim 1 wherein said slide section has a pair of parallel guides joined at one end by an end cover; and said support means mounted to slide between said guides.

3. A device as in claim 2 which comprises:
   a catch extending from said support means;
   a slot in said end cover; and
   said catch and slot arranged in operable combination with one another such that said catch engages an edge of said slat when said slide section and said support means are slid toward one another with said fabric trapped therebetween for detachable securing said device to said fabric item.

4. A device as in claim 1 wherein said means for emitting a signal includes:
   a battery;
   a signal component; and
   said battery said signal component, and said probes connected in such a way that when moisture is present in said fabric item between said probes, said signal component is activated in order to generate said signal.

5. A device as in claim 2 wherein said support means has a pair of parallel shoulders with each of said shoulders engaging one of said parallel guides respectively so that said guides slide on said shoulders.

6. A device as in claim 4 wherein said signal component emits an audible signal.

7. A device as in claim 4 wherein said signal component includes an LCD time counter.

8. A device as in claim 4 wherein said signal component includes a flashing light emitting diode.

9. A device as in claim 4 wherein said signal component includes a transmitter and a receiver remote from said transmitter such that, when moisture is present, said transmitter transmits a signal that is detected by said receiver.

10. A device as in claim 4 wherein said means for emitting a signal includes a normally closed switch connected in series with said probe such that said means for signaling is reactivated when said switch is depressed.

11. A device as in claim 1 wherein said probes have a dual function of electrical sensing as well as being pan of the mechanical lock mechanism to secure a diaper.

12. A device as in claim 3 wherein a latch on said slide section engages said catch when said slide section and said module box are in an open position to prevent accidental separation thereof.

13. A device for signaling the presence of moisture in a fabric item, said device comprising:
    a housing;
    signal emitting means retained in said housing;
    a pair of probes coupled to said signal emitting means, each of said probes having an end extending downwardly from said housing and coupled thereto, said housing supporting said probes at a predetermined distance therebetween, said signal emitting means emitting a signal responsive to conduction of electrical current between said probes;
    a slide section adapted to be slidably coupled to said housing, said slide section configured to detachably retain a portion of said fabric item between said slide section and said probe ends for detachably retaining said device on said fabric item;
    means for slidably mounting said housing on said slide section, said mounting means integrally coupled to said slide section; and
    a deflectable catch member coupled to said housing and extending outwardly therefrom, said catch member adapted to be disposed through an opening in said slide section for inhibiting said slide section from inadvertently sliding on said housing to detachably retain said device on said fabric item.

* * * * *

UNITED STATES PATENT AND TRADEMARK OFFICE
CERTIFICATE OF CORRECTION

PATENT NO. : 5,469,146
DATED : Nov. 21, 1995
INVENTOR(S) : Yener Gurler

It is certified that error appears in the above-indentified patent and that said Letters Patent is hereby corrected as shown below:

Column 2:
Line 13    disadvantage including problems with "tile" (--the--) use of safety pins;
Line 16    requirement to locate "tile" (--the--) sensor of the device inside the;
Line 54    lining that absorbs the urine and an outer "coveting" (--covering--) which is;

Column 4:
Line 38    34, and module box, 10, together securely trapping "pan" (--part--) of;

Column 6:
Line 2     "slat" (--slot--) when said slide section and said support means are;
Line 4     ebetween for "detachable" (--detachably--) securing
Claim 3:   said device to said;
Line 33    function of electrical sensing as well as being "pan"
Claim 11:  (--part--) of the;

Signed and Sealed this

Fourteenth Day of May, 1996

Attest:

BRUCE LEHMAN

*Attesting Officer*    *Commissioner of Patents and Trademarks*